United States Patent [19]

Diodati et al.

[11] Patent Number: 5,185,376
[45] Date of Patent: Feb. 9, 1993

[54] THERAPEUTIC INHIBITION OF PLATELET AGGREGATION BY NUCLEOPHILE-NITRIC OXIDE COMPLEXES AND DERIVATIVES THEREOF

[75] Inventors: Jean G. Diodati; Larry K. Keefer, both of Bethesda, Md.

[73] Assignee: The United States of America as represented by the Department of Health and Human Services, Washington, D.C.

[21] Appl. No.: 764,906

[22] Filed: Sep. 24, 1991

[51] Int. Cl.⁵ .............................. H61K 31/13
[52] U.S. Cl. ..................................... 514/611
[58] Field of Search .......................... 514/611

[56] References Cited

U.S. PATENT DOCUMENTS 4,954,526 9/1990 Keefer .................................. 514/611
5,039,705 8/1991 Keefer et al. ....................... 514/611

OTHER PUBLICATIONS

Chemical Abstracts 111:151100u, 1989.
Chemical Abstracts 114:245007h, 1991.

Primary Examiner—Leonard Schenkman
Attorney, Agent, or Firm—Birch, Stewart, Kolasch and Birch

[57] ABSTRACT

A method of inhibiting platelet aggregation in vivo with physiologically compatible compounds containing at least one N-oxo-N-nitrosoamine moiety in a molecule thereof, wherein the physiologically compatible compound releases nitric oxide in a sustained and controllable fashion in vivo.

9 Claims, 2 Drawing Sheets

THERAPEUTIC INHIBITION OF PLATELET AGGREGATION BY NUCLEOPHILE-NITRIC OXIDE COMPLEXES AND DERIVATIVES THEREOF

FIELD OF THE INVENTION

The present invention is concerned with providing a novel method of inhibiting platelet aggregation in an in vivo setting by utilizing nucleophile-nitric oxide complexes which possess at least one —$N_2O_2$— moiety and release nitric oxide in vivo in a stable and controlled fashion.

BACKGROUND OF THE INVENTION

U.S. Pat. No. 4,954,526, issued on Sep. 4, 1990, discloses stabilized nitric oxide primary amine complexes which release nitric oxide in vivo and discloses that they are useful in treating cardiovascular disorders. U.S. Pat. No. 5,039,705, issued Aug. 13, 1991, discloses anti-hypertensive compositions of secondary amine-nitric oxide adducts which release nitric oxide in vivo and that they are useful in lowering blood pressure in mammals. U.S. patent application Ser. No. 07/585,793 filed on Sep. 20, 1990, discloses complexes of nitric oxide with polyamines which release nitric oxide in vivo in a sustained and controllable fashion, and discloses that the compounds are useful in treating cardiovascular disorders. U.S. patent application Ser. No. 07/743,892, filed on Aug. 12, 1991, discloses anti-hypertensive compositions of additional secondary aminenitric oxide adducts which release nitric oxide in vivo and which are disclosed to be useful in controlling blood pressure in vivo. U.S. patent application Ser. No. 07/423,279, filed on Oct. 18, 1989, discloses anti-hypertensive compositions and methods of lowering blood pressure in mammals, which each utilize certain active compounds containing an N-oxo-N-nitrosoamine substituent, the compounds are disclosed to decompose under physiological conditions to release nitric oxide in vivo. U.S. patent application Ser. No. 07/764,908, filed Sep. 24, 1991 discloses oxygen substituted derivatives of nucleophile-nitric oxide adducts which are prodrugs for nitric oxide release in vivo and Which are useful in the treatment of cardiovascular disorders.

Each of the above disclosed U.S. patents and U.S. patent applications is incorporated herein by reference in its entirety. None of the above U.S. patents and/or U.S. patent applications discloses that the nitric oxide complexes disclosed therein inhibit platelet aggregation.

Among the most widely used clinical antiplatelet agents is aspirin, which acts by inhibiting the cyclooxygenase enzymes responsible for the arachidonic acid cascade involved in platelet aggregation (GJ Roth et al, Proc. Nat. Acad. Sci. USA 72: 3073, 1975). Although the clinical efficacy of aspirin is clear [P Théroux et al, New England J. Med. 319: 1105, 1988; ISIS-2 (2nd International Study of Impact Survival) Collaborative Group, Lancet (2): 349-360, 1988], there are important disadvantages associated with its use, such as its aggravating effect on peptic ulcers. Recently, nitric oxide has been identified as a natural messenger molecule in the inhibition of platelet aggregation via the guanylate cyclase/cyclic GMP system (BT Mellion et al, BLOOD 57:946-955, 1981).

SUMMARY OF THE INVENTION

The present invention provides for a method of inhibiting platelet aggregation in vivo. The method comprises administering to a patient in need thereof an effective platelet aggregation inhibiting amount of a physiologically compatible compound having one or more N-oxo-N-nitrosoamine (i.e., —$N_2O_2^-$) moieties in the molecule, wherein the compounds decompose in vivo to release nitric oxide in a sustained and controllable fashion.

Exemplary of the physiologically compatible compounds which are useful in the present inventive methods are the nitric oxide containing complexes disclosed in the following U.S. Pat. Nos. and U.S. patent applications:

U.S. Pat. No. 4,954,526, issued on Sep. 4, 1990;
U.S. Pat. No. 5,039,705, issued on Aug. 13, 1991;
U.S. patent application Ser. No. 07/585,793, filed on Sep. 20, 1990;
U.S. patent application Ser. No. 07/743,892, filed on Aug 12, 1991;
U.S. patent application Ser. No. 07/423,279, filed on Oct. 18, 1989; and
U.S. patent application Ser. No. 07/764,908, filed on Sep. 24, 1991.

Additionally, so long as a given compound is physiologically compatible, contains by at least one —$N_2O_2$ moiety in the molecule, and releases nitric oxide in vivo in a sustained and controllable fashion, it is also useful in the present inventive methods.

BRIEF DESCRIPTION OF THE DRAWING

The present invention will become more fully understood from the detailed description given here and below and the accompanying drawing which is given by way of illustration only, and thus is not limitative of the present invention, and wherein.

DETAILED DESCRIPTION OF THE INVENTION

Figure 1:
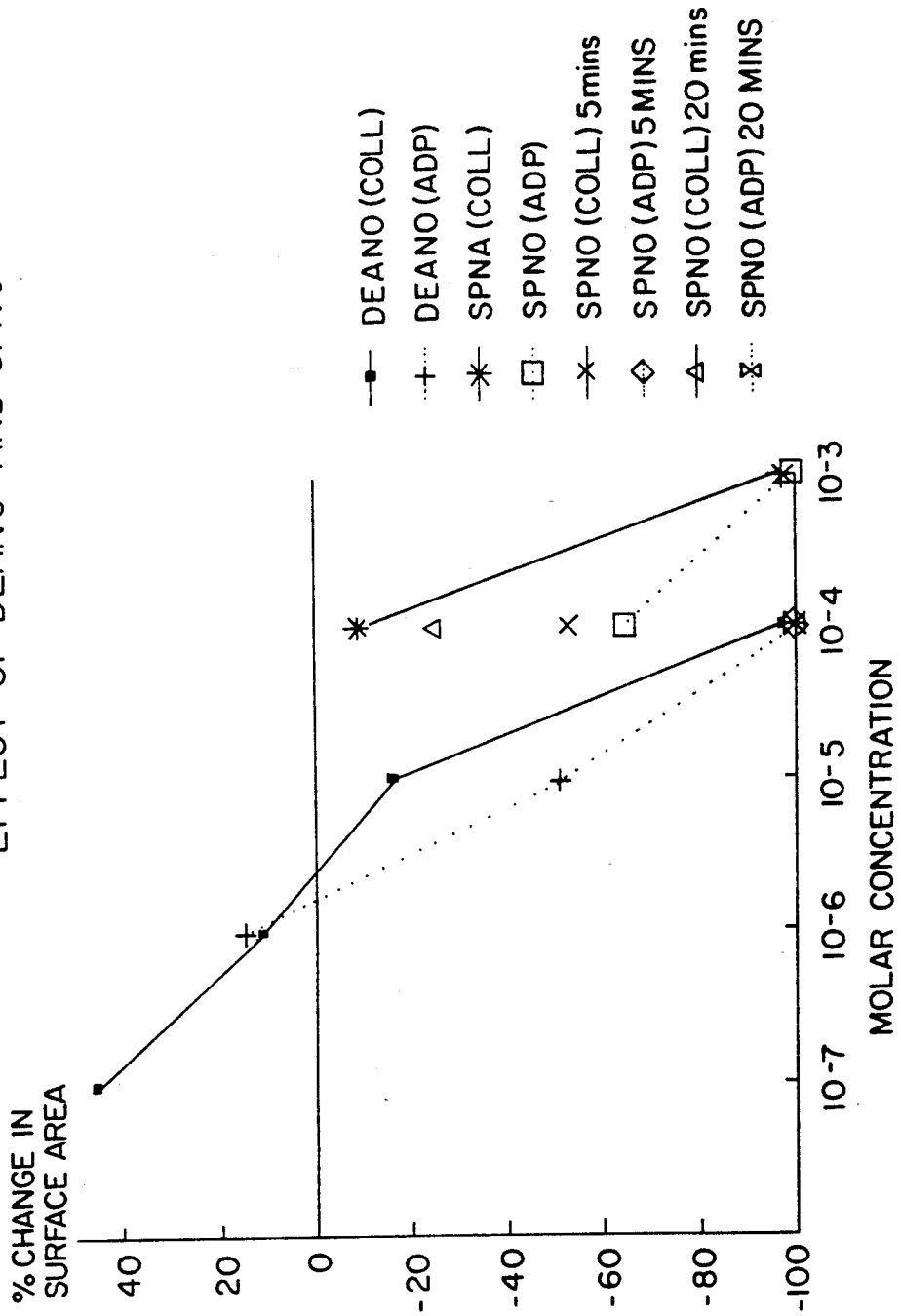
FIG. 1—Graphical representation of test results showing effect of DEANO (i.e., ($C_2H_5$)$_2$—N—N—(ONa)—N=O) and SPNO (i.e., the nitric oxide addition product of the polyamine spermine) on platelet aggregation in blood samples from donors; tests were initiated by adding COLL (i.e., Collagen) or ADP (i.e., adenosine diphosphate) to the test samples.

The following detailed description is provided as an aid to those desiring to practice the present invention. However, the same should not be deemed to unduly limit the present invention, since variations can be made in the procedures, techniques, methods, etc., disclosed herein by those of ordinary skill in the art without departing from the spirit or scope of the present inventive discovery.

Natural blood clotting depends for its success on the aggregation of the platelets ordinarily circulating as separated entities into larger masses such as platelet plugs and subsequently formed thrombi. Unfortunately, this normally beneficial process can also lead to life-threatening disorders, and overwhelming evidence now exists implicating platelet plug and thrombus formation in the pathophysiology of unstable angina, peripheral vascular disease, stroke, and myocardial infarction (MJ Davies and A Thomas, New England J. Med. 310 : 1137, 1984; E. Falk, Circulation 71 : 699, 1985; MA Dewood et al, New England J. Med. 303: 897-902, 1980). One achievement of the present invention is the provision of drugs useful in the treatment of these important causes of human death and disability. The compounds provided herein are effective in such methods of treatment due to their ability to release nitric oxide into the blood of a patient in a controlled and sustained fashion. The following Experimental Section evidences that the compounds encompassed hereby inhibit platelet aggregation in vivo.

EXPERIMENTAL

Experimental Test Procedures

Standard platelet function testing has been carried out for many years with platelet aggregometry. It is a measure of the platelets' ability to aggregate in response to a given stimulus. It has traditionally been, and still is, studied in platelet-rich plasma (PRP) with a technique involving light transmission (GVR Born, Proc. Physiological Soc., Mar. 23, 1962, 67-P). Several steps are required in the preparation of the PRP, including centrifugation and dilution. Potential drawbacks of this technique derive from the preparation of the PRP. By centrifuging the blood, sub-populations of larger platelets are lost, and the actual manipulation of the specimen could cause platelet activation, rendering them relatively refractory to stimulation by the aggregating agents.

In 1980, Cardinal and Flower (J. Pharmac. Meth. 3: 135-138, 1980) described a novel technique to measure platelet aggregation. It involves immersing a pair of platinum electrodes in a specimen with a constant current applied to them, and recording over time the change in impedance to the electrical current as an aggregating agent is added. The major advantage of this technique is that it can be carried out in whole blood. There are no preparatory steps involved. It is now a widely available and accepted technique to measure platelet function, and was the method chosen for the present Experimental Testing.

Experimental Test Results

Nine parts of human blood were drawn from the antecubital vein and mixed with on part of 3.8% sodium citrate in a plastic syringe. Donors denied taking any medication during the previous 10 days. Blood was diluted 1:1 in sterile physiologic saline. Platelet aggregation was measured at 37° C. at a pH of 7.4 using a 4-channel impedance aggregometer (Chronolog Corp.). All samples were kept at room temperature and rewarmed to 37° C. for 5 minutes before the measurement of platelet aggregation. The tests were initiated by adding either collagen (2-5 microgram/ml in the final blood:saline:drug mixture) or ADP (at a final concentration of 10-20 micromolar). Channel one of the aggregometer contained the control with no medication having been added to the blood. Channels 2, 3, and 4 contained the test agent at increasing doses ranging usually from $10^{-6}$ to $10^{-4}$ M. Blood was incubated with the drug for 1, 5, or 20 minutes before the addition of the aggregating agent.

Two nucleophile/nitric oxide complexes were studied in this way and compared to the standard clinical inhibitor, aspirin. One of the test compounds was $Et_2$-N—N(ONa)—N=O (DEANO; method of preparation is reported in Example 1a of U.S. Pat. No. 5,039,705) and the second compound was the nitric oxide addition product of the polyamine spermine (SPNO; method of preparation reported in Example 3 of U.S. patent application Ser. No. 07/585,793, filed on Sep. 20, 1990). Both test compounds contain $—N_2O_2^-$ substituents and are proved herein to be active inhibitors of platelet aggregation. Specifically, using a 1-minute delay between dosage and addition of aggregating agent, DEANO showed a 15-50% inhibition of aggregation at the $10^{-5}$ M level for both ADP and collagen, and 100% inhibition at $10^{-4}$ M. Under these conditions, SPNO was only a tenth as active as DEANO, giving 20-50% inhibition at $10^{-4}$ M and 100% at $10^{-3}$ M. The potency of SPNO could be markedly improved, however, by increasing the dosage-to-aggregation delay time from 1 minute to 5 or 20 minutes. These results, which are summarized in FIG. 1, are consistent with the view that nitric oxide release accounts for the drugs' inhibitory activity, as DEANO (halflife—2 minutes under these conditions) generates an order of magnitude more nitric oxide during the first minute of exposure than SPNO (halflife of 39 minutes) but is nearly exhausted at 5-20 minutes while SPNO continues nitric oxide generation at a more nearly constant rate during that time.

Figure 2:
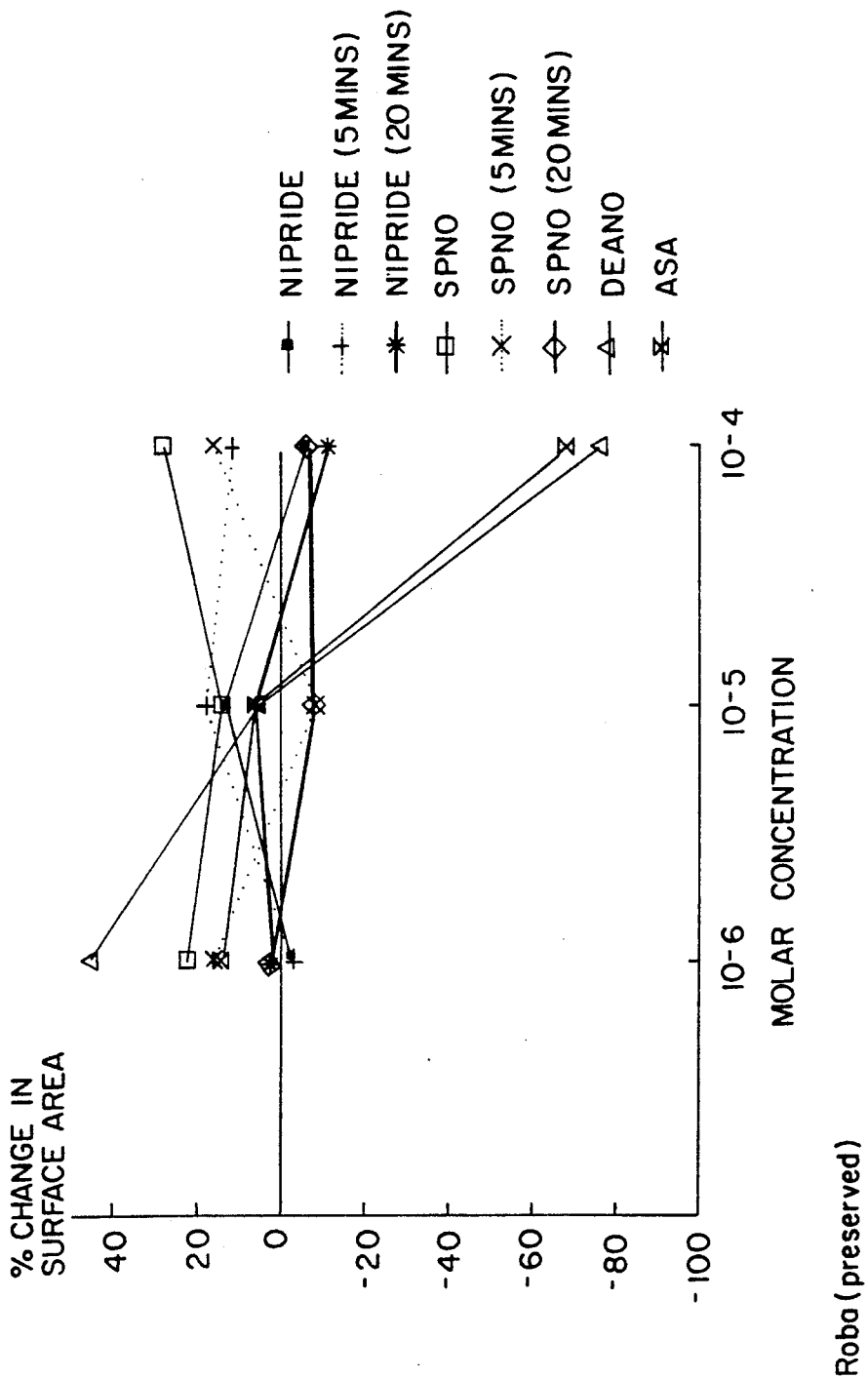
FIG. 2—provides a graphical representation of a potency comparison between DEANO (i.e., ($C_2H_5$—)$_2$ N—N(ONa)N=O), SPNO (i.e., the nitric oxide addition product of the polyamine spermine), NIPRIDE (i.e., nitroprusside) and ASA (i.e., aspirin).

FIG. 2 offers a potency comparison of DEANO and SPNO with both sodium nitroprusside (NIPRIDE) and aspirin (ASA). Neither NIPRIDE nor SPNO was active at the concentrations employed here, but DEANO proved to be at least as potent as ASA. Since aspirin is among the most effective drugs currently in use for the clinical inhibition of platelet aggregation, the fact that DEANO proved equally active in the Experimental in vitro tests utilized herein suggests that the nucleophile/nitric oxide complexes disclosed here are useful inhibitors of platelet aggregation in vivo.

PHARMACEUTICAL COMPOSITIONS

The physiologically compatible N-oxo-N-nitrosoamine containing compounds disclosed herein are preferably administered to a patient in need thereof in the form of a pharmaceutical composition, in combination with a pharmaceutically acceptable carrier. A preferred route of administration is by intravenous injection. However, the present inventive methods are not limited by the specific route of administration chosen so long as an effective dose of a physiologically compatible compound encompassed hereby is administered to a patient, and produces in the patient an inhibition of platelet aggregation. Nonetheless, a suitable dose of the compounds encompassed hereby (when administered by intravenous injection) is thought to be about 0.01 to 10.0 mg/kg/day for a given patient (e.g., a human or other mammal).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of inhibiting platelet aggregation in vivo, in a patient in need thereof, the method comprising:

administering to the patient an effective platelet aggregation inhibiting amount of a physiologically compatible compound containing at least one N-oxo-N-nitrosoamine moiety in a molecule thereof, wherein the physiologically compatible compound releases nitric oxide in vivo in a controllable and sustained fashion.

2. The method of claim 1, wherein said physiologically compatible compound is administered to the patient by intravenous injection.

3. The method of claim 2, wherein said physiologically compatible compound is administered in an amount of 0.01 to 10.0 mg/kg/day.

4. A method of inhibiting platelet aggregation in vivo, in a patient in need thereof, the method comprising:

administering to the patient an effective platelet aggregation inhibiting amount of a physiologically compatible compound which is $(C_2H_5)_2-N-N-(ONa)-N=O$, wherein the physiologically compatible compound releases nitric oxide in vivo in a controllable and sustained fashion.

5. The method of claim 4, wherein said physiologically compatible compound is administered to the patient by intravenous injection.

6. The method of claim 5, wherein said physiologically compatible compound is administered in an amount of 0.01 to 10.0 mg/kg/day.

7. A method of inhibiting platelet aggregation in vivo, in a patient in need thereof, the method comprising:

administering to the patient an effective platelet aggregation inhibiting amount of a physiologically compatible compound which is spermine bis (nitric oxide) adduct, wherein the physiologically compatible compound releases nitric oxide in vivo in a controllable and sustained fashion.

8. The method of claim 7, wherein said physiologically compatible compound is administered to the patient by intravenous injection.

9. The method of claim 8, wherein said physiologically compatible compound is administered in an amount of 0.01 to 10.0 mg/kg/day.

* * * * *